United States Patent [19]

Ferse et al.

[11] 4,072,591
[45] Feb. 7, 1978

[54] PROCESS FOR CONVERSION OF OLIGOMERS AND HIGHER POLYMERS BY IRRADIATION WITH HIGH-ENERGY ELECTRONS

[75] Inventors: Armin Ferse; Harald Grimm, both of Dresden, Germany

[73] Assignee: Akademie der Wissenschaften der Deutschen Demokratischen Republik, Berlin, Germany

[21] Appl. No.: 609,969

[22] Filed: Sept. 3, 1975

[51] Int. Cl.² .............................................. B01J 1/10
[52] U.S. Cl. ................................................. 204/159.2
[58] Field of Search ................. 204/158 HE, 162 HE, 204/159.2

[56] References Cited

U.S. PATENT DOCUMENTS

| | | | |
|---|---|---|---|
| 2,960,453 | 11/1960 | Cook et al. | 204/158 HE |
| 3,330,748 | 7/1967 | Lawton | 204/158 HE |
| 3,833,626 | 9/1974 | Ferse et al. | 204/158 HE |
| 4,029,870 | 6/1977 | Brown et al. | 204/159.2 |

OTHER PUBLICATIONS

Modern Plastics, vol. 37, No. 4, Dec. 1959, pp. 144, 145, 148, 224 & 225.

*Primary Examiner*—Howard S. Williams
*Attorney, Agent, or Firm*—Michael J. Striker

[57] ABSTRACT

Processes for the production of products containing fluorine-containing compounds of lower molecular weight by irradiation with high-energy electrons of a dispersion of particles of solid polymers of tetrafluoroethylene and similar perfluoroolefins in an oligomer of the same or a different perfluoroolefin which is liquid at the reaction temperature and having a lower average molecular weight than the solid perfluoroolefin polymers while passing an inert or reactive gas therethrough, and an apparatus in which such processes can be performed.

16 Claims, 1 Drawing Figure

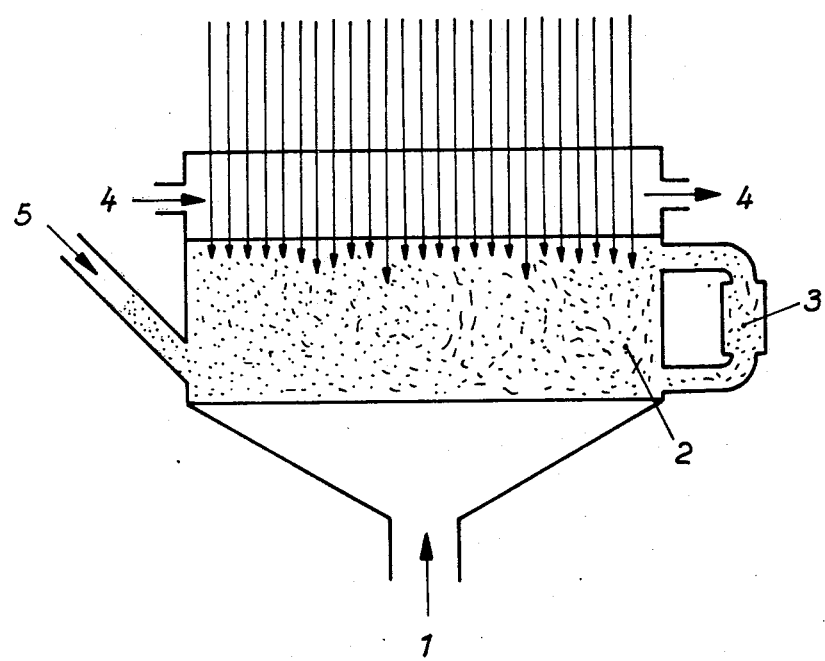

PROCESS FOR CONVERSION OF OLIGOMERS AND HIGHER POLYMERS BY IRRADIATION WITH HIGH-ENERGY ELECTRONS

BACKGROUND OF THE INVENTION

The present invention pertains to processes and apparatus for the chemical conversion of solid polymers of tetrafluoroethylene and similar perfluoroolefins into useful fluorine-containing compounds of lower molecular weight by irradiation of the solid polymer with high-energy electrons in the presence of an inert or reactive gas.

The term perfluoroolefin as used herein is to be understood to include also perfluoroolefins in which one of the fluorine radicals has been replaced by a radical of another halogen such as chlorotrifluoroethylene.

It is known that, in order to depolymerize or react solid polymers of tetrafluoroethylene and similar perfluoroolefins with an inert or reactive gas in a zone that is irradiated with high-energy electrons, the solid polymers must be brought into intimate contact with the gas within the irradiation zone in the form of a powder. This is generally achieved by bringing the gases into contact with the surfaces of the particles of the powder or by passing the gases through a mass of the powder. In both cases, however, optimal contact between the gas and the solid particles cannot be achieved since, in the first place, the ratio of the surface area of the solid to its total volume is small and, in the second case, a so-called tunneling or formation of essentially unobstructed passages through the mass of powder generally occurs.

Irradiating particles of the solid polymer while it is suspended in the gas appears at first glance to be an ideal method of promoting such reactions. However, polytetrafluoroethylene when bombarded with or irradiated with high-energy electrons passes through several successive allotropic modifications or forms, namely, from a filamentous or feltlike form through a flourlike or powdery form, and finally to a viscous liquid form resembling honey, which thus also introduces other problems and difficulties that cannot be avoided in such processes.

Furthermore chemical reactions that are initiated and promoted by actinic or ionizing radiations, such as high-energy electrons, produce cleavage, substitution, and interchange reactions so that the resulting products are mixtures of compounds having widely differing compositions and molecular weights.

Polytetrafluoroethylenes can be decomposed or cleaved by heat or by the action of other forms of energy into oligomers of lower molecular weight and monomers. In attempts to obtain a complete conversion, however, the mass, as a rule, was completely decomposed, producing fluorine, cokelike substances, and various other fluorine-containing decomposition compounds.

Perfluoroolefins, especially perfluoroethylenes such as tetrafluoroethylene, can at present only be produced by conventional methods of synthesis. There is nevertheless an increasing demand for highly reactive compounds having high contents of fluorine and low molecular weight that are suitable for the production of perfluoroalkanoic and similar perfluorocarboxylic and perfluoroalkanesulfonic acids which are of great interest and importance for the production of textile auxiliaries, surfactants, biologically active substances and other valuable industrial chemical products. The fluorine-containing compounds are significantly superior with respect to their effects as well as their properties to related nonfluorinated compounds and they are further characterized by their great thermal and chemical stability, their incompatibility with water and oils, and their outstanding surface characteristics.

SUMMARY OF THE INVENTION

In the processes of the present invention, dispersions of particles of solid perfluoroolefin polymers such as polytetrafluoroethylene, polyhexafluoropropylene, and solid copolymers of tetrafluoroethylene and hexafluoropropylene, in oligomers of perfluoroolefins which have lower average molecular weights than the solid perfluoroolefin polymers and are liquid at the reaction temperature are irradiated with beams of high-energy electrons while a stream of an inert or reactive gas is passed or bubbled therethrough. The volatile product that is thus formed, which consists essentially of a relatively homogeneous mixture of fluorine-containing compounds that have approximately the same molecular weights, is continuously carried out of the irradiation zone and recovered.

The processes of the present invention provide an advantageous method for depolymerizing and converting solid particles of perfluoroolefins, especially tetrafluoroethylene and hexafluoropropylene and solid copolymers of tetrafluoroethylene and hexafluoropropylene, by bombardment with high-energy electrons and treatment with inert gases or gaseous reagents. Solid polymers of perfluoroolefins cannot readily react with gaseous reagents because of the difficulty of bringing the gaseous reagent into intimate contact with the solid, as referred to hereinbefore.

In the processes of the present invention the reactions occur only at the top surface and uppermost portions of the dispersion through which the high-energy electrons penetrate to a depth of only about 2 millimeters.

Surprisingly, the product that is formed when a dispersion of particles of a solid polytetrafluoroethylene having an average molecular weight above 1,000,000 in a liquid oligomer of polytetrafluoroethylene having an average molecular weight of 1000 is bombarded with beams of high-energy electrons while a stream of a reactive gas is passed therethrough consists essentially of a mixture of fluorine-containing compounds that have nearly the same molecular weights.

The perfluoroethylene oligomer having an average molecular weight of approximately 1000 can be made by preliminary bombardment of the solid perfluoroethylene polymer with high-energy electrons and is normally liquid at the temperature at which the dispersion of the solid polyperfluoroethylene therein is maintained while the gas is passed therethrough. By dispersing the particles of the solid polyperfluoroethylene in the liquid oligomer, the difficulties that are associated with the treatment of solid particles thereof by suspending them in the gas or passing the gas therethrough is avoided.

The flow rate and pressures of the gases that are passed through the dispersion of the solid polyperfluoroolefin particles in the liquid perfluoroolefin oligomer are varied so as to keep the solid particles homogeneously distributed therein. The composition and temperature of the gas are adjusted so as to provide optimal conditions for promoting the desired conversions.

The flow rate and pressure of the gas stream may also be varied so as to carry off all of the conversion products or, when a second stream of the same or a different gas is also used for carrying off the conversion products, the flow rates and pressures of the two streams may be coordinated with respect to each other in order to maintain optimal conditions.

The mixtures of fluorine-containing compounds that are produced in accordance with the processes of the present invention are surprisingly homogeneous and are composed of compounds which have substantially the same molecular weight, even when the dispersion that is irradiated or bombarded with high-energy electrons includes a plurality of components having widely differing molecular weights, for example, solid polytetrafluoroethylene having an average molecular weight of 1,000,000 and liquid polytetrafluoroethylene having an average molecular weight of 1000. The molecular weights of the products can be varied however by varying the temperature at which the substances are irradiated with the high-energy electrons.

The conversion products are carried along with the gas stream that is passed or bubbled through the fluid dispersion and are frozen or condensed by cooling beyond the zone in which the dispersion was irradiated. The boiling points of the products that are thus carried along corresponds approximately to the temperature at which the dispersion of solid particles was irradiated.

When the gas that is used is pure nitrogen, for example, which itself does not react with the polymer that is irradiated, the conversion products of polytetrafluoroethylenes that are formed at an irradiation temperature of 120° C are straight-chain perfluoroolefins and perfluoroparaffins having from 6 to 9 carbon atoms per molecule. At an irradiation temperature of 170° C the conversion products have from 8 to 11 carbon atoms and, at an irradiation temperature of 250° C, the conversion products have from 11 to 16 carbon atoms.

If the gas that is used contains oxygen, which reacts with polytetrafluoroethylenes, carbonyl fluoride, which has a boiling point of −83° C, and normal acyclic perfluorocarboxylic acids are formed. The number of carbon atoms that are included in the molecules of the resulting normal acyclic perfluorocarboxylic acids is dependent upon the irradiation temperature and these acids will have, for example, an average of 4, 7, or 12 carbon atoms per molecule when the temperatures during the irradiation are maintained at respectively 120°, 170°, and 250° C.

In the processes of the present invention, useful fluorine-containing compounds can be obtained when the temperature of the dispersion during the irradiation and treatment with the gas is maintained within the range between 120° and 300° C but such temperatures are to be understood to be a preferred range to which the invention is not restricted.

Gaseous reagents which are especially suitable for use in the processes of the present invention are those which under the selected reaction conditions are capable of being activated or converted to a moiety resembling a radical or themselves react as a free radical, such as, for example, molecular oxygen ($O_2$), nitric oxide (NO), nitrogen dioxide ($NO_2$), halogens, such as chlorine, sulfur dioxide ($SO_2$), carbon monoxide (CO), and carbonyl fluoride ($COF_2$).

Although dispersions consisting of solid and liquid homopolymers of the same perfluoroolefin are referred to herein and in the examples, the processes are applicable to the treatment of dispersions in which either or both the solid and liquid polymers themselves may be copolymers of different perfluoroolefins as illustrated in Example 3 hereinafter, as well as mixtures of homopolymers of different perfluoroolefins.

A large number of fluorine-containing organic compounds and fluorochemicals, including fluorocarbons, perfluoroalkanes, perfluorocarboxylic and perfluoroalkanesulfonic acids can, by selection of suitable gaseous reagents, be produced directly in accordance with the processes of the present invention or can be produced from the perfluoroolefin conversion products that are produced when an inert gas such as nitrogen is used in accordance with the processes of the present invention.

DESCRIPTION OF THE DRAWING

An apparatus is represented in the accompanying drawing which is suitable for carrying out the processes of the present invention. In this apparatus the material that is to be irradiated with high-energy electrons is subjected to irradiation in the form of a dispersion of solid particles in a liquid. The electrons are supplied from above the fluidized bed. This apparatus includes an inlet for gases beneath the dispersion, an inlet and outlet for passing gases across the surface of the dispersion and an inlet for charging sidewise into the apparatus the material that is to be irradiated. A sensor is also provided in the dispersion for actuating devices for controlling the temperature thereof.

DETAILED DESCRIPTION AND PREFERRED EMBODIMENTS OF THE INVENTION

The invention is further described and illustrated in connection with the examples which follow, which were selected solely for purposes of illustration and consequently are not to be construed as restrictive of the invention or its scope.

EXAMPLE 1: APPARATUS

The apparatus that was used in the examples which follow, which is represented in the accompanying drawing, consisted of a reactor 1 for receiving and confining the fluid dispersion that was irradiated, which dispersion was charged thereinto through an inlet 2. The upper portion of this reactor 1 was closed with a sheet material or screen 3 that was previous to high-energy electrons but impervious to gases so that the surface and upper portions of the fluid dispersion in the reactor could be bombarded or irradiated with such electrons from above. The bottom of the reactor was formed of a sheet material 4 that was pervious to gases. The reactor was also provided with an inlet 5 for gases that was located below the bottom 4 of the reactor. The gases were charged through the inlet 5 at a pressure sufficient to retain the fluid dispersion in the reactor and prevent it from leaking or flowing through the pervious bottom sheet 4 of the reactor. The reactor was also provided with a gas inlet 6 for supplying a carrier gas above the surface of the fluid dispersion in the reactor to sweep out the reacting products as formed together with any unreacted gases that had passed through the fluid dispersion in the reactor. An outlet 7 was provided for discharging the carrier gas and volatile products from the reactor.

The reactor was also provided with a bypass 8 in which was located a sensor 9 that was connected to other devices that are not shown to actuate such devices and thereby control the temperature and the flow of the gas through the dispersion in the reactor.

The dispersion that is to be irradiated, consisting of particles of the solid perfluoroolefin polymer dispersed in the liquid perfluoroolefin oligomer of lower molecular weight, is charged into the reactor through the inlet 2 in the direction shown by the arrow. This dispersion is then irradiated from above with beams of high-energy electrons from a conventional electron generator. A stream of gas, whose temperature, flow rate, composition, and pressure have each been adjusted to preselected values for the particular operation of the process to produce a desired product, is then charged upwardly from the inlet 5 through the dispersion 2.

The resulting product, which is volatile under the preselected reaction conditions and which consist essentially of a homogeneous mixture of compounds having nearly the same molecular weights, is then carried off with the original gas stream that had passed through the dispersion or preferably with a second stream of an inert gas that was charged through the inlet 6 in the direction indicated by the arrows across the surface of the dispersion in the reactor and through its outlet 7. The composition, temperature, flow rate and pressure of this second stream of gas can likewise be varied to suit individual requirements. The dispersion is charged into the reactor through the inlet 2 at such a rate as to compensate for quantities of the dispersion that are converted and discharged from the reactor in the form of a volatile product and thereby also maintain a desired level in the reactor.

EXAMPLE 2

Particles of a solid tetrafluoroethylene having an average molecular weight of 1,000,000 were dispersed in a liquid polytetrafluoroethylene having an average molecular weight of 1000 that was preliminarily produced by depolymerizing some of the same solid polytetrafluoroethylene by bombarding or irradiating it with high-energy electrons. This dispersion was then charged in the form of a continuous stream into a reactor, such as described hereinbefore in Example 1, and represented in the accompanying drawing, through the inlet 2 so as to fill the reactor chamber with the liquid dispersion to a suitable level and thereafter to compensate only for that amount that was withdrawn therefrom as volatile product in order to maintain a preselected level of the dispersion in the reactor.

A stream of a hot gas was bubbled or blown from below into the body of the liquid dispersion while the dispersion was bombarded or irradiated from above with beams of high-energy electrons and the body of the liquid dispersion was maintained at a temperature of 120° C that was controlled by means of a sensor 9. The conversion product together with any portions of the initial hot gas that had not reacted with components of the dispersion were carried out of the apparatus by a stream of nitrogen or other inert carrier gas which was passed over and above the surface of the fluid dispersion in the apparatus. The products were isolated from the carrier gas by cooling so as to condense or freeze the conversion products.

When the gas that was bubbled through the suspension was nitrogen, and the irradiated body of the liquid dispersion was maintained at a temperature of 120° C, the conversion product consisted essentially of a mixture of depolymerized polytetrafluoroethylenes comprising essentially normal perfluoroalkanes and straight-chain perfluoromonoolefins and straight-chain perfluoropolyolefins having from 6 to 9 carbon atoms per molecule. When the temperature was maintained at 170° C, the conversion product consisted essentially of a mixture of the same type of compounds which however, had 8 to 11 carbon atoms per molecule and consequently had a higher average molecular weight. When the temperature was maintained at 250° C, the conversion product consisted essentially of the same type of compounds which however had from 11 to 16 carbon atoms per molecule.

When the gas that was passed through the suspension consisted of a mixture of nitrogen and oxygen in the volume ratio of 93 : 7, respectively, and the iradiation was effected while the body of the fluid dispersion was maintained at a temperature of 120° C, the conversion product consisted of gaseous carbonyl fluoride and a mixture consisting essentially of acid fluorides of normal perfluorocarboxylic acid having an average of 4 carbon atoms per molecule.

When iraddiated and maintained at a temperature of 170° C, the conversion product consisted essentially of a mixture of the same type of compounds having an average of 7 carbon atoms per molecule and, at a temperature of 250° C, a mixture of the same type of compounds having an average of 12 carbon atoms per molecule. These products are used for example for treating porous or non-porous substrates preferably to achieve oleophobic finishes on fibrous materials, such as textiles and paper.

EXAMPLE 3

An apparatus such as that represented in the accompanying drawing was filled to a suitable level with a dispersion of solid particles of polytetrafluoroethylene having an average molecular weight of over 1,000,000 distributed in a liquid copolymer of tetrafluoroethylene and hexafluoropropylene having an average molecular weight of 8000 whose composition corresponded to 9 molecules of tetrafluoroethylene per molecule of hexafluoropropylene. Additional quantities of the dispersion were supplied continuously through the inlet to compensate for those quantities thereof that were converted and withdrawn from the reactor as volatile reaction products.

While the temperature of the dispersion in the reactor was maintained at 160° C, and the dispersion was irradiated with beams of high-energy electrons, a stream of hot air was charged upwardly therethrough at such a rate that the solid particles in the dispersion were maintained homogeneously distributed therein.

A stream of nitrogen gas was used to carry off the unreacted air and volatile products which were recovered as described hereinbefore in Example 2.

In this Example, the oxygen of the air was the reagent, and the conversion products consisted of carbonyl fluoride and a mixture of acid fluorides of straight-chain perfluorocarboxylic acids having 7 to 11 carbon atoms per molecule, a portion of which consisted of acid fluorides of straight-chain perfluorocarboxylic acids having methyl side chains. These products are used, for example, as surface active agents having special properties.

EXAMPLE 4

Into an apparatus such as that described in Example 1 containing a dispersion of particles of a solid polytetrafluoroethylene has an average weight of 1,000,000 in a liquid partially depolymerized polytetrafluoroethylene having an average molecular weight of 1000 that was produced by partial depolymerization of a solid polytetrafluoroethylene was continuously charged a stream of a mixture of 90 parts by volume of nitrogen to 10 parts by volume of nitric oxide (NO). The dispersion was maintained in the apparatus at a temperature of 130° C while it was bombarded with a stream of accelerated electrons having a kinetic energy of 1.2 million electron volts. The volatile reaction products were carried out of the apparatus with a stream of nitrogen gas into a cooling apparatus in which the lessvolatile products were condensed and frozen while fresh quantities of the dispersion were continuously supplied to replace quantities that had thus been converted to other products and withdrawn from the reactor.

The product that was thus produced was a turquoise-colored unctuous greasy solid that had an average molecular weight of 450. Its elementary analysis indicated it to be composed of carbon, fluorine, 1.9% by weight of nitrogen, and 2.0% by weight of oxygen.

EXAMPLE 5

Example 4 was repeated with the same dispersion of solid polytetrafluorethylene in the liquid polytetrafluoroethylene but the dispersion was maintained at a temperature of 160° C instead of 130° C and the gas that was passed therethrough consisted of a mixture of 80 parts by volume of nitrogen, 10 parts by volume of chlorine, and 10 parts by volume of sulfur dioxide.

The product in this example comprised sulfur hexafluoride and a viscous liquid whose elementary analysis indicated it to consist of carbon, fluorine, 3.5% by weight of chlorine, 3.5% by weight of sulfur, and 3.2% by weight of oxygen.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A process for the production of a fluorine-containing compound of lower molecular weight from a solid polymer of a perfluoroolefin which comprises irradiating with a beam of high-energy electrons at a temperature of between substantially 120–300° C a dispersion of particles of the said solid perfluoroolefin polymer distributed in a perfluoroolefin polymer which is liquid at the reaction temperature and having a lower average molecular weight than the solid perfluoroolefin polymer while a gas that is inert to or reactive with the perfluoroolefin polymers is passed upwardly therethrough so that reactions occur only in the uppermost portions of the dispersion at and directly below the upper surface thereof, and recovering the fluorine compounds that are thus produced.

2. A process as defined in claim 1 in which the solid perfluoroolefin is a hompolymer of tetrafluoroethylene or hexafluoroethylene or a mixture thereof or a copolymer of tetrafluoroethylene and hexafluoroethylene.

3. A process as defined in claim 1 in which the liquid perfluoroolefin is a homopolymer of tetrafluoroethylene or hexafluoroethylene or a mixture thereof or a copolymer of tetrafluoroethylene and hexafluoroethylene.

4. A process as defined in claim 1 in which the solid polymer of the perfluoroolefin has an average molecular weight of the order of 1,000,000.

5. A process as defined in claim 1 in which the polymer of the perfluoroolefin which is liquid at the reaction temperature has an average molecular weight of the order of 1000.

6. A process as defined in claim 1 in which the perfluoroolefin which is liquid at the reaction temperature is a copolymer of tetrafluoroethylene and hexafluoropropylene having an average molecular weight of the order of 8000.

7. A process as defined in claim 1 in which the inert gas is nitrogen.

8. A process as defined in claim 1 in which the reactive gas is molecular oxygen, nitric oxide, nitrogen dioxide, a halogen, sulfur dioxide, carbon monoxide or carbonyl fluoride.

9. A process as defined in claim 1 in which the reactive gas is molecular oxygen.

10. A process as defined in claim 1 in which the reactive gas is nitric oxide.

11. A process as defined in claim 1 in which the reactive gas is nitrogen dioxide.

12. A process as defined in claim 1 in which the reactive gas is chlorine.

13. A process as defined in claim 1 in which the reactive gas is sulfur dioxide.

14. A process as defined in claim 1 in which the reactive gas is carbon monoxide.

15. A process as defined in claim 1 in which the reactive gas is carbonyl fluoride.

16. A process as defined in claim 1 in which the reactive gas is a mixture of nitrogen, chlorine, and sulfur dioxide.

* * * * *